(12) United States Patent
Li

(10) Patent No.: US 9,850,383 B2
(45) Date of Patent: Dec. 26, 2017

(54) UNCHARGED PYRENYLOXY SULFONAMIDE DYES FOR CONJUGATION WITH BIOMOLECULES

(71) Applicant: Yongfu Li, Corvallis, OR (US)

(72) Inventor: Yongfu Li, Corvallis, OR (US)

(73) Assignee: Gene Tools, LLC, Philomath, OR (US)

( * ) Notice: Subject to any disclaimer, the term of this patent is extended or adjusted under 35 U.S.C. 154(b) by 0 days.

(21) Appl. No.: 14/998,651

(22) Filed: Jan. 27, 2016

(65) Prior Publication Data
US 2017/0210904 A1    Jul. 27, 2017

(51) Int. Cl.
*C07H 19/20* (2006.01)
*C09B 57/00* (2006.01)
*G01N 21/64* (2006.01)

(52) U.S. Cl.
CPC ....... *C09B 57/001* (2013.01); *G01N 21/6486* (2013.01)

(58) Field of Classification Search
None
See application file for complete search history.

(56) References Cited

U.S. PATENT DOCUMENTS

| | | | |
|---|---|---|---|
| 5,132,432 | A | 7/1992 | Haugland et al. |
| 7,470,420 | B2 | 12/2008 | Singaram et al. |
| 8,394,357 | B2 | 3/2013 | Singaram et al. |
| 2009/0305410 | A1* | 12/2009 | Mao .............. C09B 11/08 435/375 |

OTHER PUBLICATIONS

Bjorn Finkler et al., Highly photostable "super"—photoacids for ultrasensitive flourescence spectroscopy, journal, Jan. 14. 2014.

* cited by examiner

*Primary Examiner* — Patrick T Lewis
(74) *Attorney, Agent, or Firm* — Teri G. Andrews

(57) ABSTRACT

The invention relates to novel fluorescent dyes based on the following pyrenyloxy sulfonamide structure:

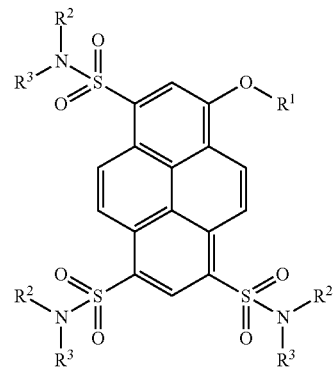

wherein $R^1$ is a leash joined to the pyrenyloxy group via an ether link containing generally a reactive functional group such as, activated carbonate, activated ester, amino group, azide or alkyne for conjugation with biomolecules; $R^2$ and $R^3$ are hydrogen atoms, or short alkyl chains, or cyclic rings with or without heteroatoms such as nitrogen, oxygen, sulfur, phosphorus. The spectral properties of the fluorescent dyes are sufficiently different in wave-lengths and intensity from fluorescein as to permit simultaneous use of fluorescein and/or more other fluorescent dyes with minimum interference and to avoid interference from endogenous green fluorescent protein in biological system. The dyes are non-ionic to facilitate their entry into cells for intracellular detection. The non-ionic structure also precludes undesired electrostatic reactions with ionic sites on biological components and structures. The dyes have bigger Stokes' shifts than other dyes with similar spectral properties allowing use of simpler, more efficient detection equipment, are not sensitive to pH, and have good solubility in aqueous solution.

11 Claims, 8 Drawing Sheets

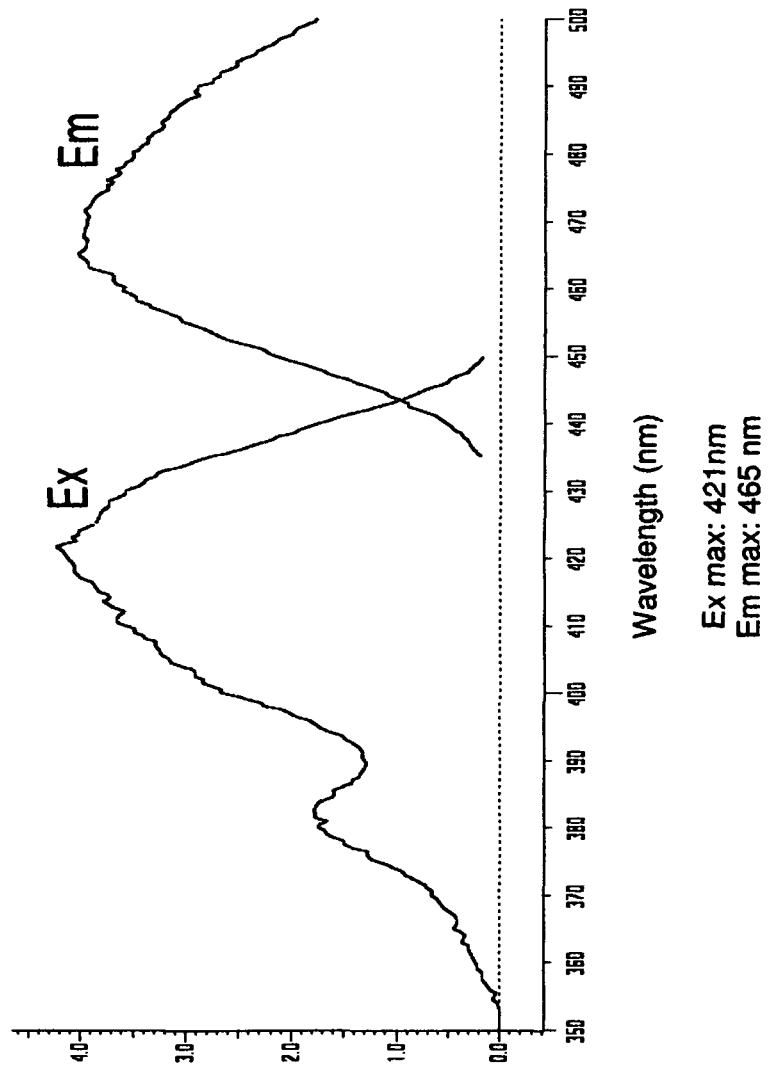

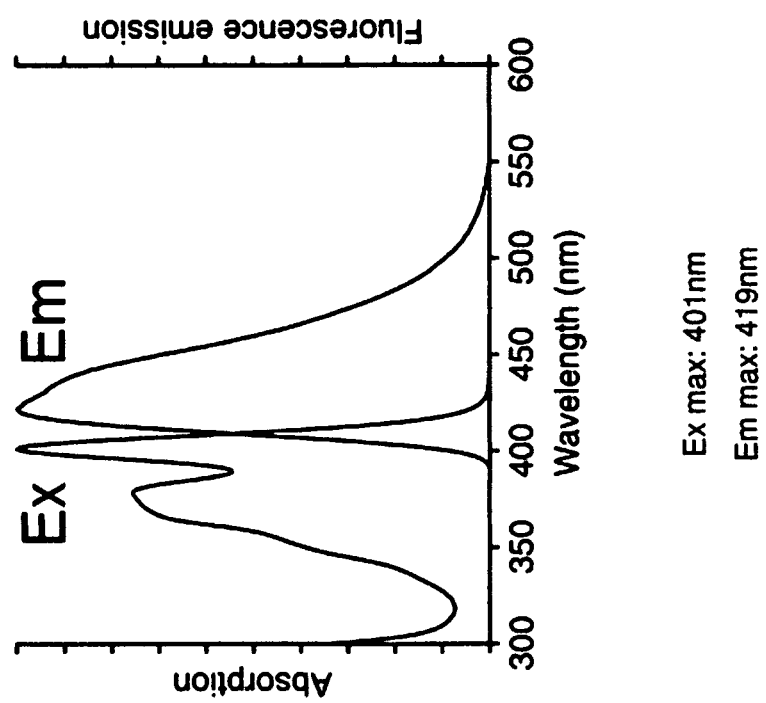
Figure 2. Excitation and Emission Spectrum of Cascade Blue

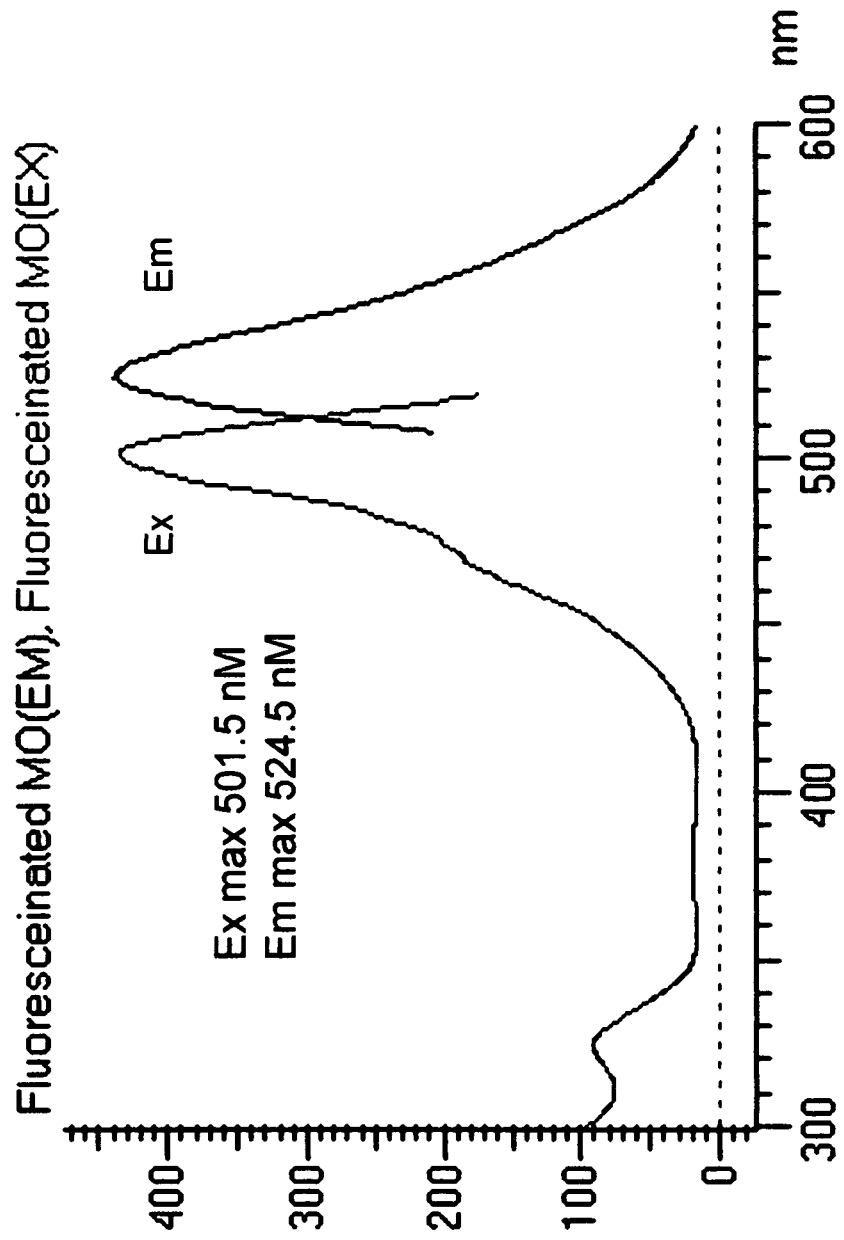
Figure 3. Excitation and Emission Spectrum of Fluorescein

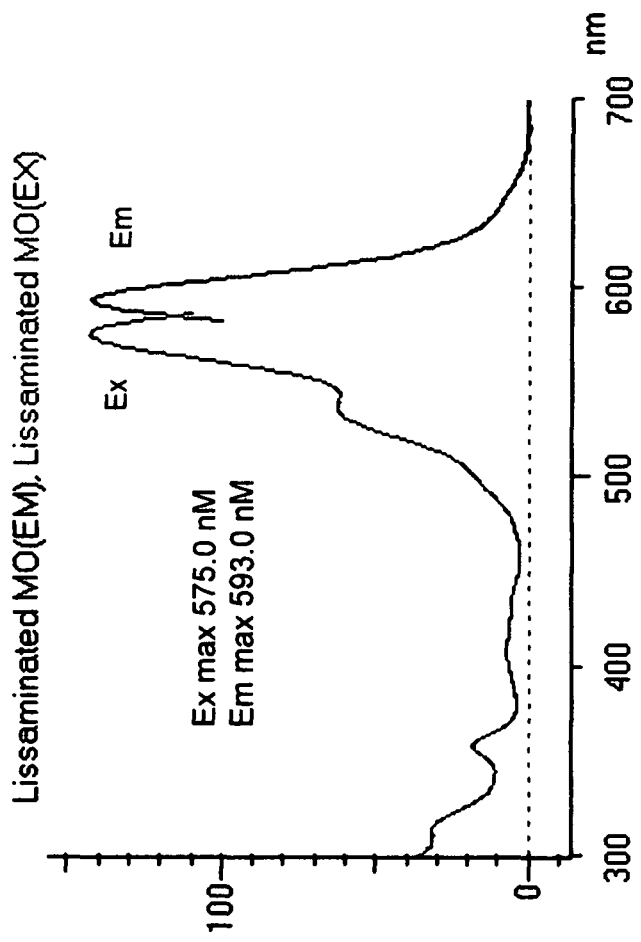
Figure 4. Excitation and Emission Spectrum of Lissamine

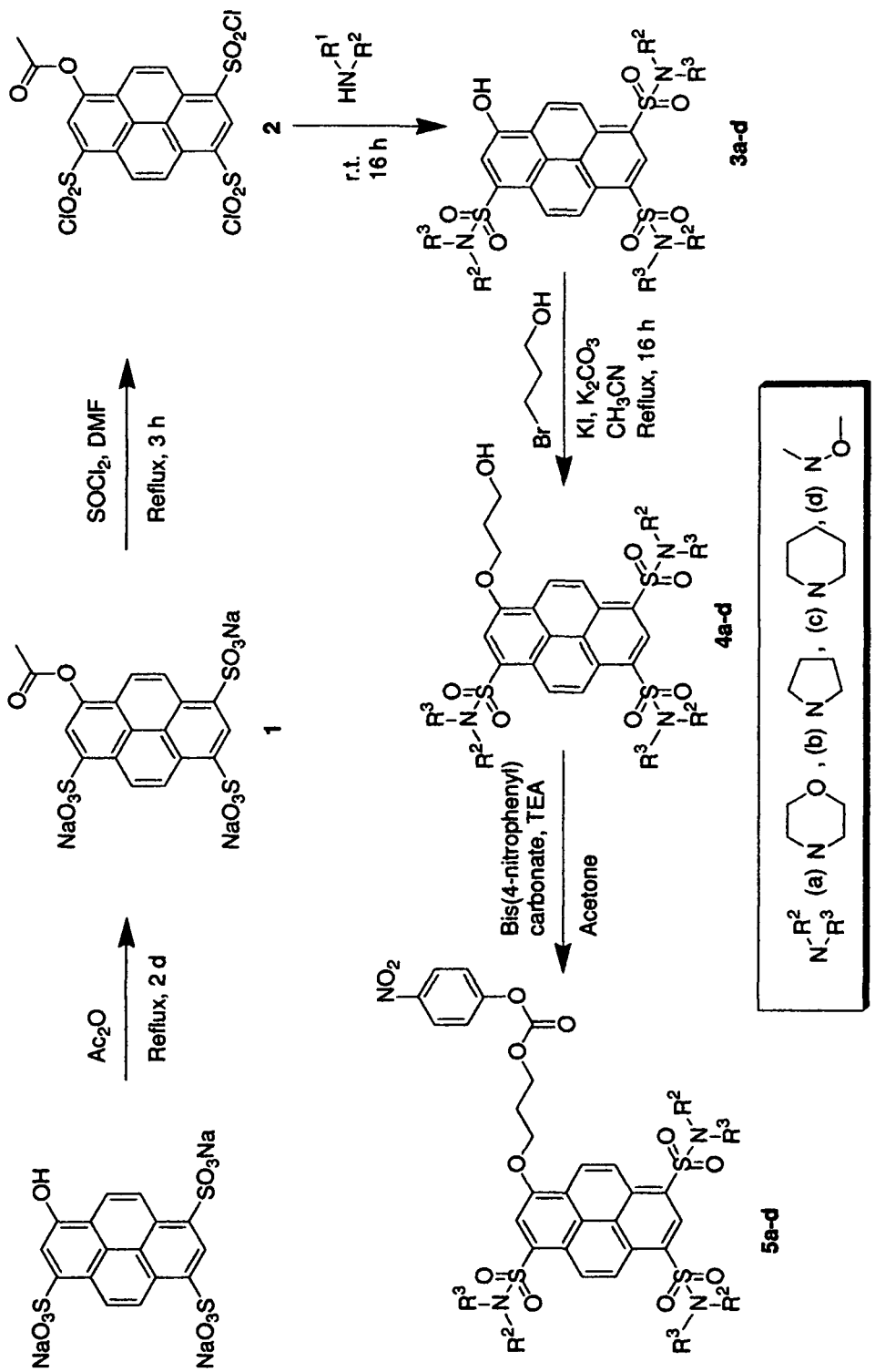
Figure 5 Synthesis of Activated Carbonate of Pyrenyloxy Sulfonamide

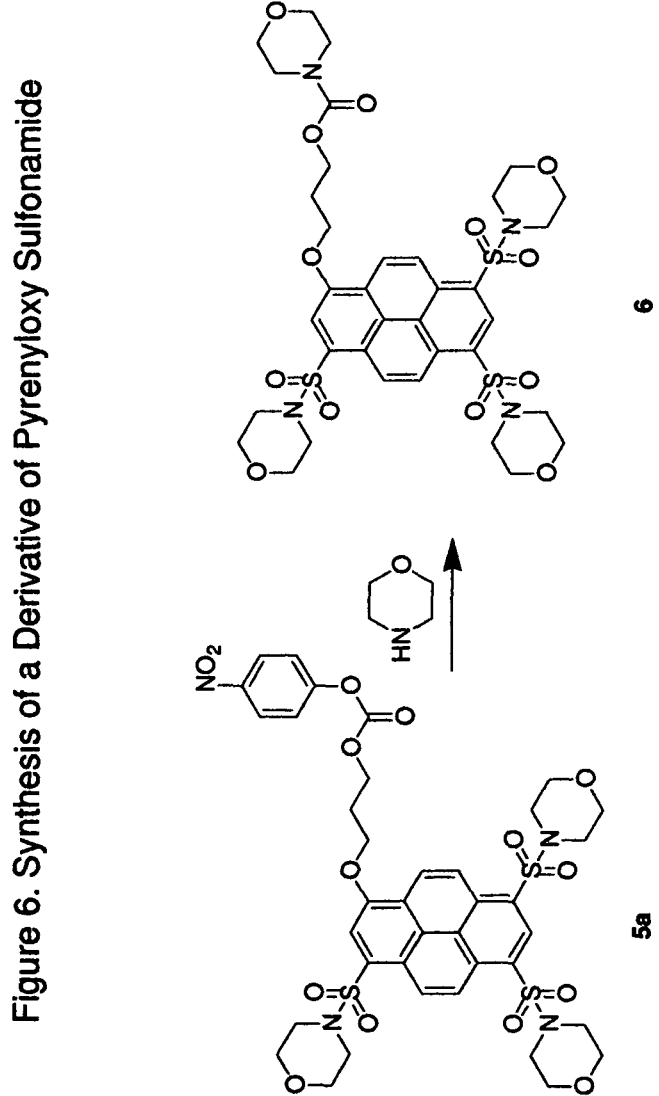
Figure 6. Synthesis of a Derivative of Pyrenyloxy Sulfonamide

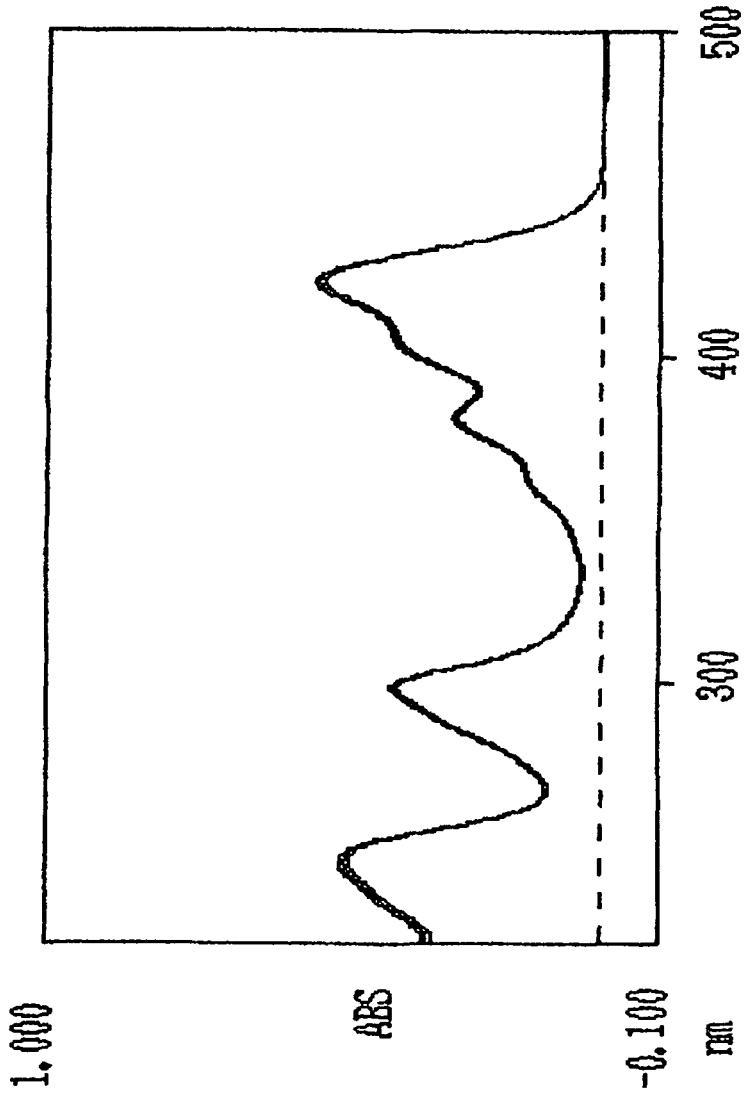
Figure 7. Photostability test of pyrenyloxy sulfonamide derivative (Compound 6)
The spectra are a collection of overlaid sequential scans up to 60 minutes with 15 minute interval.

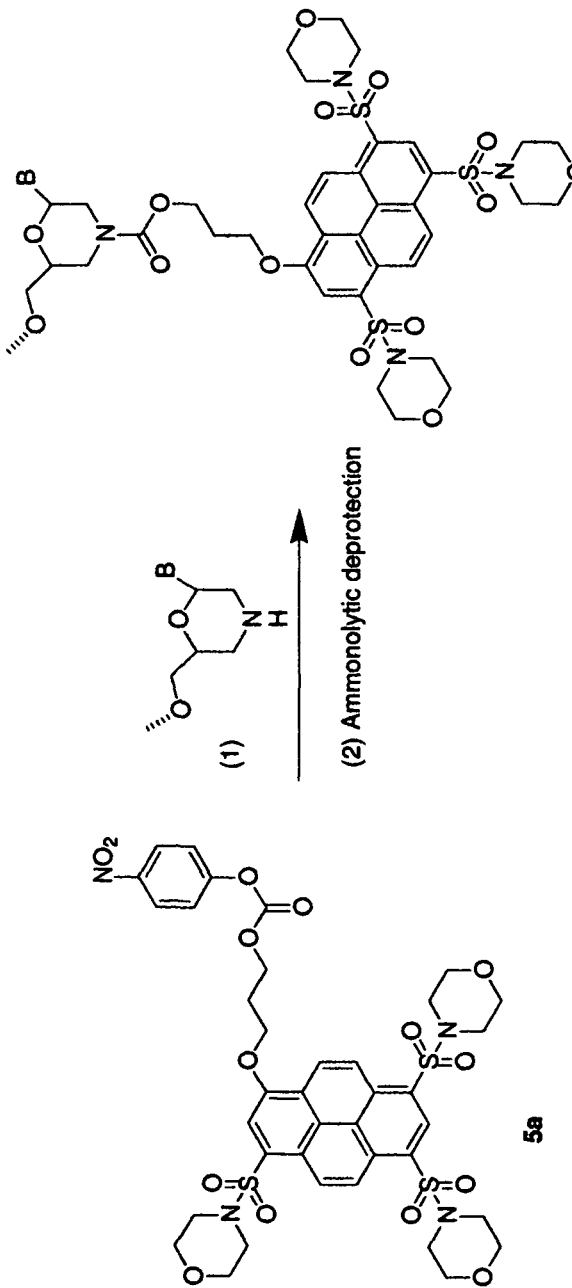
Figure 8. Synthesis of a Morpholino Conjugate with a Pyrenyloxy Sulfonamide Dye

US 9,850,383 B2

UNCHARGED PYRENYLOXY SULFONAMIDE DYES FOR CONJUGATION WITH BIOMOLECULES

FIELD OF THE INVENTION

This invention is related to improvements in dyes useful as fluorescent tracers. Specifically the improvements relate to non-ionic pyrenyloxy sulfonamide dyes that are joined with a leash containing a reactive functional group which can be conjugated to biomolecules. The conjugate with a biomolecule is sufficiently different in wave-lengths and intensity from fluorescein as to permit simultaneous use of fluorescein and/or more other fluorescent dyes with minimum interference and to avoid interference from endogenous green fluorescent protein in biological system.

BACKGROUND OF THE INVENTION

Fluorescent dyes are widely used as tracers for localization of biological structures by fluorescence microscopy, for quantification of analytes by fluorescence immunoassay, for flow cytometric analysis of cells, for measurement of physiological state of cells and other applications. Their primary advantages over other types of absorption dyes include the visibility of emission at a wavelength distinct from the excitation, the orders of magnitude greater detectability of fluorescence emission over light absorption, the generally low level of fluorescence background in most biological samples and the measurable intrinsic spectral properties of fluorescence polarization, life-time and excited state energy transfer.

For many applications that utilize fluorescent dyes as tracers, it is necessary to chemically react the dye with a biologically active component, such as a cell, tissue, protein, antibody, enzyme, or a biomolecule such as a drug, hormone, nucleotide, nucleic acid, polysaccharide, lipid or other biomolecules, to make a fluorescent composite or to react the dye with natural or synthetic macromolecules or polymers. With these synthetic probes, the biomolecule frequently confers a specificity for a biochemical interaction that is under investigation and the fluorescent dye provides the method for detection and/or quantification of the interaction. Chemically reactive synthetic fluorescent dyes have long been recognized as essential for tracking these interactions. It is often desirable to employ a fluorescent dye which is significantly different from the background fluorescence, such as a protein which has green fluorescence to avoid interference. It is also frequently desirable to employ more than one fluorescent conjugate simultaneously and to quantify the conjugates independently, requiring selective detection of each fluorescent probe. It is also desirable that the dye does not have negative charges or positive charges so that it does not impede entry into cells for detecting the interactions inside the cell. The dyes in common use are limited to a relatively small number of aromatic structures. It is an object of this invention to provide fluorescent tracers which can be used to the green fluorescein background or in conjunction with fluorescein and other commonly used fluorescent probes. It is further an object of this invention to provide dyes with the chemical reactivity necessary for conjugation to the functional groups commonly found in biomolecules, drugs, and natural and synthetic macromolecules or polymers. It is further an object of this invention to provide dyes whose fluorescence has low sensitivity to solution pH, whose composition has high solubility in aqueous medium, and whose structure has no negative or positive charges to allow approach to the cell surface or access to the cell entry.

Virtually all fluorescence microscopes are equipped with excitation sources and filters optimized to excite and detect fluorescein emission. Fluorescein has broad emission in the visible portion of the spectrum beginning at approximately 480 nm, peaking at about 514 nm and decreasing to 10% of the peak intensity at approximately 580 nm (FIGS. 3 and 4). However, the commonly used green fluorescent protein in some cases causes interference as the background noise. There is a need for suitable fluorophores which can shift away from the green emission wavelength region to avoid the interference with fluorescein and with green fluorescent protein. And there is also a recognized need for suitable fluorophores for applications in multi-color microscopy, flow cytometry, immnoassays, and DNA sequencing. Since fluorescein has essentially no fluorescence below 490 nm, there is a clear opportunity to detect suitable fluorophores that have strong emission below this wavelength (FIG. 1). The desirable dyes would have the following properties:

1. A high fluorescence quantum yield with a reasonably narrow emission band at wavelengths sufficiently shorter than that of fluorescein so the longest wavelength components of the dye emission have minimal spectral overlap with the fluorescein emission band.
2. A high absorptivity as measured by extinction coefficient. Preferred are dyes that can be excited with the most intense emission lines of the common excitation sources such as the 365 nm line or longer. Excitation shorter than 365 nm is less desirable since it can result in cell injury or death in applications where fluorescence measurements are performed on living cells. Furthermore, auto-fluorescence of proteins, nucleic acids and other biomolecules present in cells is also increased with shorter wavelength excitation. Use of wavelengths longer than 350 nm also permits use of less expensive glass optics instead of quartz optics.
3. High solubility of the dye and its reactive derivatives in aqueous solution to enhance the utility of the dye for modification of cells, biopolymers, macromolecules and other biomolecules to be used in an aqueous environment.
4. High stability of the dye to excitation light, enhancing the utility of the dye for quantitative measurements and permitting extended illumination time and higher lamp intensities without significant photobleaching.
5. For quantitative measurements, low sensitivity of the emission intensity to properties of the solution is necessary so that the measured signal is proportional only to the absolute quantity of dye present and is independent of environmental effects such as pH, viscosity and polarity.
6. Suitability of the dye for preparation of reactive derivatives of several different types which exhibit reactivity toward a variety of chemically reactive sites.
7. Intrinsically low biological activity or toxicity of the dye.
8. The non-ionic structure of the dye, which avoids undesired electrostatic interactions with other components of the system.

Pyrene derivatives such as pyrene-1-butyrate is quite lipophilic and insoluble in the aqueous solution. The property of low aqueous solubility hinders the fluorescent labeling of proteins, polysaccharides and other biomolecules, thereby making it practically unusable in consequent biological application. The Cascade Blue (Haugland et al. U.S. Pat. No. 5,132,432), a commercially available sulfonated pyrene derivative, has three negative charges whose anionic character compromises cell membrane-permeability which can only be used extracellularly. A need clearly exists for new fluorescent dyes that have good aqueous solubility and in particular a non-ionic structure that can be used for both intracellular and extracellular detection. The high solubility of the pyrenyloxy sulfonamide dyes, that are the subject of this invention, results in fluorescent derivatives that are highly water soluble. This uncharged nature of the molecule and high aqueous solubility of the dyes enhance their usefulness as fluorescent tracers for hydrophilic environments and increase their suitability for use in applications requiring not only extracellular detection, but also intracellular detection. This solubility property also facilitates the coupling, in aqueous solution, of the fluorescent dye with a protein, drug, or other component of interest.

In conclusion, the dyes which are the subject of this invention exhibit all of the desirable properties described above, namely:
1. Large Stokes' shifts (over 40 nm).
2. Little spectral overlap with fluorescein.
3. High extinction coefficient.
4. Excellent photostability.
5. High water solubility.
6. Low sensitivity to pH.
7. Reactivity with many of the functional groups found in biomolecules.
8. Compatibility with common excitation sources.
9. Uncharged structure useful for extracelluar, and more importantly, intracellular detection.

SUMMARY OF THE INVENTION

The subject materials of this invention have fluorescence properties sufficiently different from fluorescein and green fluorescent protein that they can be used in the presence of either of these materials in biological systems, or concurrently with fluorescein based tracers. They show low sensitivity of fluorescence emission to pH, and the uncharged structural feature of the dye is useful to allow staining the cell surface, and allow intracellular detection. These reactive derivatives posses no ionic charges and their reactive forms and conjugates have excellent solubility in water and other highly polar solvents.

BRIEF DESCRIPTION OF THE DRAWINGS

FIG. 1. Excitation and emission spectrum of pyrenyloxy sulfonamide (Compound 4a)
FIG. 2. Excitation and emission spectrum of Cascade Blue
FIG. 3. Excitation and emission spectrum of fluorescein
FIG. 4. Excitation and emission spectrum of lissamine
FIG. 5. Synthesis of activated carbonate of pyrenyloxy sulfonamide
FIG. 6. Synthesis of pyrenyloxy sulfonamide derivative (Compound 6)
FIG. 7. Photostability test of Compound 6
FIG. 8. Synthesis of a Morpholino conjugate with a pyrenyloxy sulfonamide dye

DETAILED DESCRIPTION OF THE INVENTION

The core structure of the improved, reactive, hydrophilic, uncharged fluorophores is a new class of pyrenyloxy sulfonamide compounds. This invention describes methods for the synthesis of novel derivatives with substantially improved properties, as well as demonstration that the materials can be chemically bonded to the functional groups present in many biomolecules to form fluorescent conjugate. The novelty of this invention involves the substantial improvement of the properties of Cascade Blue, a currently available blue-fluorescent dye. The high polarity of anionic sulfonate of Cascade Blue results in the membrane-impermeability which can only be used extracellularly, a major disadvantage for many desirable applications. The uncharged fluorophores of this invention do not impede cell entry. And the high aqueous solubility of the pyrenyloxy sulfonamide is useful for biological and physiological application, allowing staining the cell surface which is negatively charged, and even more useful to enter the cell for intracellular detection. In addition, the Stokes shift of Cascade Blue is undesirably small (ca. 20 nm, FIG. 2). It is highly desirable to increase the Stokes Shift so that the signal to noise ratio can be substantially improved. The Stokes shift of the compounds of this invention is a much more practical 44 nm (FIG. 1), a significant improvement in its utility as a tracer for biological applications. The molar extinction coefficient of the structure of the invention is slightly higher ($3.1 \times 10^4$ cm$^{-1}$ M$^{-1}$ at $\lambda 423$ nm) than that of Cascade Blue ($2.9 \times 10^4$ cm$^{-1}$ M$^{-1}$ at $\lambda 410$ nm), an additional advantage for increased sensitivity. Photostability of the dye (compound 6 in FIG. 6) was tested under the light exposure. The scans were overlaid up to 60 mins with 15 min interval. FIG. 7 shows the robust stability of the core structure of the dye of this invention. This resistance to photobleaching greatly enhances the utility of the dye for quantitative measurements and permits extended illumination time.

Pyrenyloxy sulfonamide compounds, namely the phenol intermediates (analogous to Compound 3 in FIG. 5) were reported in literature (Finkler B. et al: Photochem. Photobiol. Sci. 2014, 13, 548-562). However, those compounds were used as end products for fluorescence spectroscopic studies. The phenolic moiety or other sites of the molecule were not further derivatized to install a leash containing a reactive functional group, lacking the function for covalent conjugation with biomolecules. Two filed patents [(Singaram B. and Wessling R. A. U.S. Pat. No. 7,470,420 and U.S. Pat. No. 8,394,357)] did not describe the installation of the reactive functional groups for conjugation with biomolecules, making them only useful for staining as dyes, not a tracer for the conjugate of the biomolecule of the interest. Reactive functional groups were installed in this invention which are useful to form covalent linkage with many of the functional groups found in biomolecules. Potentially reactive functional groups that are intrinsically present or that can be introduced into the pyrenyloxy sulfonamide compounds which can conjugate with biomolecules and macromolecules include but are not limited to activated carbonate, amines, thiols, alcohols, carboxylic acids, activated esters, aldehydes, ketones, azides, alkynes or constrained cycloalkynes. Chemically reactive fluorescent reagents developed in this invention are generally very mild for conjugation with biomolecules, and thus will be useful not only for modification of the synthetic macromolecules, but also for the biologically active ligands such as a cell, tissue, protein, antibody, enzyme, or a biomolecule such as a drug, hormone, nucleotide, nucleic acid, polysaccharide, lipid or other biomolecules such as natural macromolecules or polymers. None of the reagents previously described in the chemical or biochemical literature are recognized as possessing the appropriate combination of chemical reactivity, spectral properties, high water solubility, non-ionic structural feature, fluorescence yield and lack of pH sensitivity to make them optimum for use in the presence of background green fluorescent protein, or for simultaneous use with one or more than one fluorescent dyes.

The new pyrenyloxy sulfonamide derivatives that are the subject of this invention have the general structure below.

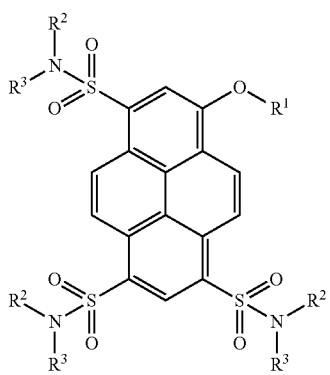

In this structure, $R^2$ and $R^3$ are hydrogen atoms, or short alkyl chains, or cyclic rings with or without heteratoms such as nitrogen, oxygen, sulfur, phosphorus to confer the sulfonamide with uncharged feature under physiological conditions and appropriate water solubility.

$NR^2R^3$:

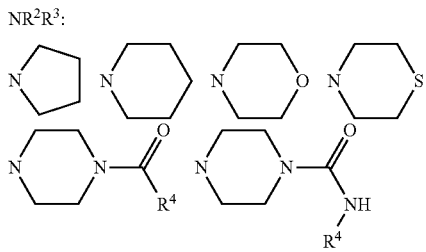

$R^2$, $R^3$, $R^4$=H, $CH_3$, $C_2H_5$, $CH_2CH_2CH_3$, $CH_2CH_2OR^4$, $CH_2CH_2NHCOR^4$

Furthermore, $R^1$ is a leash that can be further modified to provide a chemically reactive functional group. The subsequent modifications include but are not limited to chemically reactive derivatives such as activated carbonate, and activated carboxylic acids such as p-nitrophenyl esters, pentafluorophenyl esters, succinimidyl esters, acyl azides, and acid halides, or other reactive groups that include acrylamides, alkyl and arylazides, alkynes and constrained cyclic alkynes, anhydrides, halides, sulfonate esters, amine and hydrazine derivatives, alcohols, haloacetamides, isothiocyanates and isocyanates.

Several representative examples of derivatives that have the chemical structure and properties claimed by this invention and the precursors that are used in their synthesis are illustrated below. It should be clearly recognized that the leash length and structural architecture can vary as long as the reactive functional groups are constructed which can be used for conjugation with macromolecules and biomolecules. The listing is not meant to be inclusive of chemical reactivity since with the appropriate choice of solvent, temperature and catalysts, other functional groups can be made to react and the listed functional groups can be made to react with other reactive moieties.

$OR^1$:

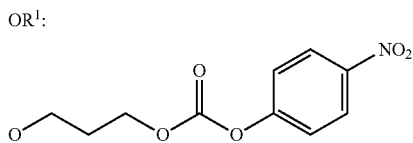

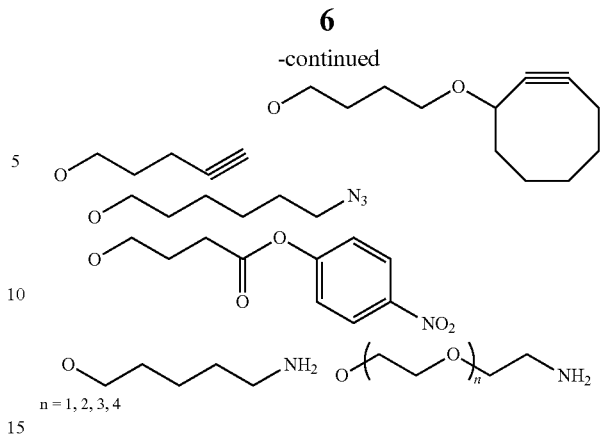

Chemically reactive derivatives of fluorophores have wide utility as tracers. This invention describes methods for preparation of pyrenyloxy sulfonamide dyes that incorporate activated carbonate as shown in FIG. 5. Acetylation of trisodium 8-hydroxypyrene-1,3,6-trisulfonic acid protects the phenolic hydroxyl to give the corresponding acetate 1. Trisulfonyl chloride 2 was converted from trisulfonate sodium salt with thionyl chloride. Trisulfonamide 3 formation by treatment with a secondary amine resulted in concomitant generation of phenolic alcohol providing the substrate for phenolic alkylation. The alkyl leash with a terminal hydroxyl group 4, after exposed to bis(4-nitrophenyl) carbonate, furnishes an activated carbonate moiety 5, useful for conjugation with biomolecules. An example was shown by using the activated carbonate of pyrenyloxy sulfonamide dye of this invention to conjugate a Morpholino oligo (FIG. 8). The conjugation was carried out while the oligo was still on the synthesis resin. The conjugate was obtained by the global ammonolytic deprotection of the protecting groups of the Morpholino subunits and the cleavage from the synthesis resin. The process provides a practical means for efficient streamlined production of conjugate containing the pyrenyloxy sulfonamide dye of this invention and a biomolecule such as a Morpholino oligo.

Other reactive functional groups include, but not limited to carboxylic acids and esters, amines, hydrazides, halides, alcohols and aldehydes and their subsequent modification to give chemically reactive reagents that can be coupled to other molecules for use as fluorescent tracers.

The excitation and emission spectrum of compound 4a is shown in FIG. 1. Obvious is the spectra region shorter than 500 nm which is particularly valuable to get away from interference where green fluorescent protein is present or, to carry out the applications requiring multiple dyes such as flow cytometry, DNA sequencing and multiparameter microscopy. More remarkable is the significantly greater Stokes' shift (ca. 44 nm) of the pyrenyloxy sulfonamide dye (peak of excitation: 421 nm, peak of emission: 465 nm). This special feature increases the sensitivity of the fluorescence techniques where the emission signal can be maximized against the low background.

EXAMPLES

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The following synthetic examples illustrate how one of ordinary skill in the art could synthesize a variety of chemically reactive derivatives containing the desired fluorophore that are the subject of this invention. The methods outlined are intended to be illustrative and not to define or limit the possible methods of dye synthesis. It is also to be recognized that the specific compounds described herein are included for the purpose of clearly demonstrating the nature of the invention and do not exhaust the structural and chemical variations which are also considered to fall within the scope of this invention. It is to be understood that certain changes and modifications which are apparent to one skilled in the art are included in the purview and intent of this invention. Inclusion of spectral and other characterization of some of the synthetic products and intermediates is intended to facilitate comparison and confirmation of products by one skilled in interpretation of spectral techniques and not to specifically define limitations or absolute values for physical properties of the materials.

A general scheme for synthesis of several pyrenyloxy sulfonamide dyes that are or can be modified to have the desired chemical reactivity or chemical substituents falling within the scope of this invention is illustrated below. The general method consists of condensation of an alkylating reagent such as an alkyl halide or appropriately substituted alkyl halide, in the presence of a base with a substituted pyrene sulfonamide 3 having a hydroxyl on the 8-position to give an alkoxy intermediate such as compound 4 in FIG. 5.

Frequently, there are a number of alternative routes whose choice depends primarily on the availability (or ease of synthesis) of the reactants, solvents and equipment. Suitable bases for the initial alkylation step include but are not limited to bicarbonate, carbonate, diisopropylethylamine, and triethylamine. Suitable catalysts for the initial alkylation step include but are not limited to potassium iodide, tetrabutylammonium iodide. Suitable substituents on the alkylating reagent include but are not limited to substituted or unsubstituted alkyl, cycloalkyl, arylalkyl and aryl derivatives. Pyrenyloxy sulfonamide products may be modified in subsequent reactions by known chemical techniques including but not limited to esterification, sulfonation, nitration, alkylation, acylation, and halogenation. Furthermore, the substituents can in some cases be further modified to introduce chemically reactive functional groups, or biologically active groups that are understood to fall within the scope of this patent. Examples of methods that are suitable for preparation of selected members of this new class of reactive dyes are given in the examples outlined below. It is recognized that variations in the synthetic methods and reactants are possible that would fall within the scope and intent of this invention.

Example 1

Trisodium 8-acetoxypyrene-1,3,6-trisulfonic acid (1)

Trisodium 8-hydroxypyrene-1,3,6-trisulfonic acid (4.56 g, 8.70 mmol) and sodium acetate (71.4 mg, 0.88 mmol) were suspended in acetic anhydride (50 ml) and refluxed for 35 hours (Finider, B. et al. *Photochemical & Photobiological Sciences* 13, 548-562 (2014)). After the suspension was cooled down to room temperature, it was diluted with THF and filtered off. The residue was washed with acetone and dried under vacuum yielding a grey powder (5.52 g, 8.0 mmol, 92%).

Example 2

8-Acetoxypyrene-1,3,6-trisulfonyl chloride (2)

The above trisulfonic acid 1 (1.09 g, 1.93 mmol) was suspended in thionyl chloride (5 ml). After addition of dimethylformamide (30 µl), the mixture was heated to reflux for 5 hours. The solution was cooled down to room temperature and poured on ice. After precipitation, the sulfonyl chloride was filtered off and was obtained as an orange powder after drying in vacuo (1.04 g, 1.88 mmol, 97%).

Example 3

8-Hydroxypyren-tris(morpholino)-1,3,6-trisulfonamide (3a)

The above trisulfonyl chloride 2 (1.04 g, 1.88 mmol) was added to morpholine (10 ml) cooled in an ice bath. The mixture was kept at room temperature for 16 hours. Most reagents were removed by evaporation. The residue was dissolved in dichloromethane and washed with aqueous hydrochloric acid (1N). The organic layer was separated and dried over sodium sulfate. After removal of the solvent, the residue was obtained as orange powder (1.20 g, 1.80 mmol, 95%). $R_f$=0.11 (ethyl acetate/hexanes: 1/1).

8-Hydroxypyren-tris(pyrrolidino)-1,3,6-trisulfonamide (3b)

Compound 3b was prepared following the general procedure as for 3a. The product was obtained as orange powder (98%). $R_f$=0.26 (ethyl acetate/hexanes: 1/1).

8-Hydroxypyren-tris(piperidino)-1,3,6-trisulfonamide (3c)

Compound 3c was prepared following the general procedure as for 3a. The product was obtained as orange powder (97%). $R_f$=0.45 (ethyl acetate/hexanes: 1/1).

8-Hydroxypyren-N,N',N''-trimethoxy-N,N',N''-trimethyl-1,3,6-trisulfonamide (3d)

Compound 3d was prepared following the general procedure as for 3a. N,O-Dimethylhydroxylamine hydrochloride was deprotonated with triethylamine and reacted with the trisulfonyl chloride 2. The product was obtained as orange powder (90%). $R_f$=0.38 (ethyl acetate/hexanes: 1/1).

Example 4

8-(3'-hydroxypropyloxy)pyren-tris(morpholino)-1,3,6-trisulfonamide (4a)

The above 8-hydroxypyrene derivative 3a (1.20 g, 1.80 mmol) was dissolved in acetonitrile (20 ml). 3-Bromopropanol (278 mg, 2 mmol), potassium carbonate (690 mg, 5 mmol) and potassium iodide (10 mg, 0.06 mmol) were added to the mixture. The mixture was kept at 80° C. for 16 hours. After removal of the solvent, the residue was dissolved in dichloromethane and washed with water. The organic layer was dried over sodium sulfate and evaporated to give a solid as yellow powder (1.07 g, 1.48 mmol, 82%). $R_f$=0.25 (ethyl acetate/hexanes: 3/1).

8-(3'-hydroxypropyloxy)pyren-tris(pyrrolidino)-1,3,6-trisulfonamide (4b)

Compound 4b was prepared following the general procedure as for 4a. The product was obtained as yellow powder (80%). $R_f$=0.08 (ethyl acetate/hexanes: 1/1).

8-(3'-hydroxypropyloxy)pyren-tris(piperidino)-1,3,6-trisulfonamide (4c)

Compound 4c was prepared following the general procedure as for 4a. The product was obtained as yellow powder (77%). $R_f$=0.20 (ethyl acetate/hexanes: 1/1).

8-(3'-hydroxypropyloxy)pyren-N,N',N"-trimethoxy-N,N',N"-trimethyl-1,3,6-trisulfonamide (4d)

Compound 4d was prepared following the general procedure as for 4a. The product was obtained as yellow powder (83%). $R_f$=0.22 (ethyl acetate/hexanes: 1/1).

Example 5

8-[3'-(4"-nitrophenoxycarbonyloxypropyloxy)]pyren-tris(morpholinyl)-1,3,6-trisulfonamide (5a)

The above 3'-hydroxypropyloxypyrene derivative 4a (1.07 g, 1.48 mmol) was dissolved in acetone (20 ml). Bis(4-nitrophenyl) carbonate (912 mg, 3 mmol) and triethylamine (1 ml) were added to the solution. The mixture was kept at room temperature for 16 hours. After removal of the volatile materials, the residue was dissolved in dichloromethane and loaded on a silica gel column. The product was isolated by chromatography to give a yellow solid (1.20 g, 1.35 mmol, 91%). $R_f$=0.73 (ethyl acetate/hexanes: 3/1).
$^1$H-NMR (400 MHz, CDCl$_3$): δ=9.33 (d, 1H, J=9.94), 9.30 (d, 1H, J=9.68), 9.27 (s, 1H), 9.16 (d, 1H, J=9.94), 8.92 (d, 1H, J=9.58), 8.38 (s, 1H), 8.28 (d, 2H, J=9.24), 7.40 (d, 2H, J=9.21), 4.72 (t, 2H, J=6.20), 4.67 (t, 2H, J=5.87), 3.75 (m, 12H), 3.26 (m, 12H), 2.60 (m, 2H).

8-[3'-(4"-nitrophenoxycarbonyloxypropyloxy)]pyren-tris(pyrrolidino)-1,3,6-trisulfonamide (5b)

Compound 5b was prepared following the general procedure as for 5a. The product was obtained as yellow solid (88%). $R_f$=0.39 (ethyl acetate/hexanes: 1/1).
$^1$H-NMR (400 MHz, CDCl$_3$): δ=9.36 (d, 1H, J=9.98), 9.31 (d, 1H, J=9.68), 9.21 (s, 1H), 9.18 (d, 1H, J=9.74), 8.87 (d, 1H, J=9.66), 8.43 (s, 1H), 8.28 (d, 2H, J=9.16), 7.41 (d, 2H, J=9.15), 4.72 (t, 2H, J=6.13), 4.65 (t, 2H, J=5.93), 3.50 (m, 4H), 3.48 (m, 4H), 3.44 (m, 4H), 2.58 (m, 2H), 1.94 (m, 8H), 1.86 (m, 4H).

8-[3'-(4"-nitrophenoxycarbonyloxypropyloxy)]pyren-tris(piperidino)-1,3,6-trisulfonamide (5c)

Compound 5c was prepared following the general procedure as for 5a. The product was obtained as yellow solid (96%). $R_f$=0.54 (ethyl acetate/hexanes: 1/1).
$^1$H-NMR (400 MHz, CDCl$_3$): δ=9.28 (d, 1H, J=9.95), 9.27 (d, 1H, J=9.64), 9.24 (s, 1H), 9.13 (d, 1H, J=10.29), 8.87 (d, 1H, J=9.58), 8.39 (s, 1H), 8.29 (d, 2H, J=9.15), 7.41 (d, 2H, J=9.19), 4.72 (t, 2H, J=5.88), 4.64 (t, 2H, J=6.05), 3.30 (m, 4H), 3.29 (m, 4H), 3.24 (m, 4H), 2.58 (m, 2H), 1.64 (m, 12H), 1.48 (m, 6H).

8-[3'-(4"-(4"-nitrophenoxycarbonyloxypropyloxy)]pyren-N,N',N"-trimethoxy-N,N',N"-trimethyl-1,3,6-trisulfonamide (5d)

Compound 5d was prepared following the general procedure as for 5a. The product was obtained as yellow solid (93%). $R_f$=0.41 (ethyl acetate/hexanes: 1/1).
$^1$H-NMR (400 MHz, CDCl$_3$): δ=9.52 (d, 1H, J=9.48), 9.47 (d, 1H, J=10.02), 9.35 (d, 1H, J=10.05), 9.35 (s, 1H), 8.95 (d, 1H, J=9.82), 8.41 (s, 1H), 8.28 (d, 2H, J=9.17), 7.40 (d, 2H, J=9.21), 4.72 (t, 2H, J=6.24), 4.66 (t, 2H, J=5.90), 3.80 (s, 3H), 3.78 (s, 3H), 3.73 (s, 3H), 2.98 (s, 3H), 2.97 (s, 3H), 2.59 (m, 2H).

Example 6

Determination of the Chemical Reactivity of the Dye and Conjugation with a Morpholino Oligo The chemical reactivity of the dyes that are the subject of this invention was determined by incubation of the reactive derivatives 5a in dimethylsulfoxide solution with a model Morpholino Oligo where the oligo is still on the synthesis resin. After incubation at 50° C. for 4 hours, the conjugate is then treated with concentrated ammonia to remove the protecting groups on the oligo subunits and to cleave the conjugate from the synthesis resin. It was demonstrated that the reactive dye derivative can be efficiently coupled with the Morpholino oligo while still on the synthesis resin, making the process in a practical manner where the excessive reactive dye can be removed by washing with the solvent, and the conjugate (structure shown below) can be obtained by deprotection of protecting groups of the oligo subunits and cleavage of the oligo conjugate from the synthesis resin.

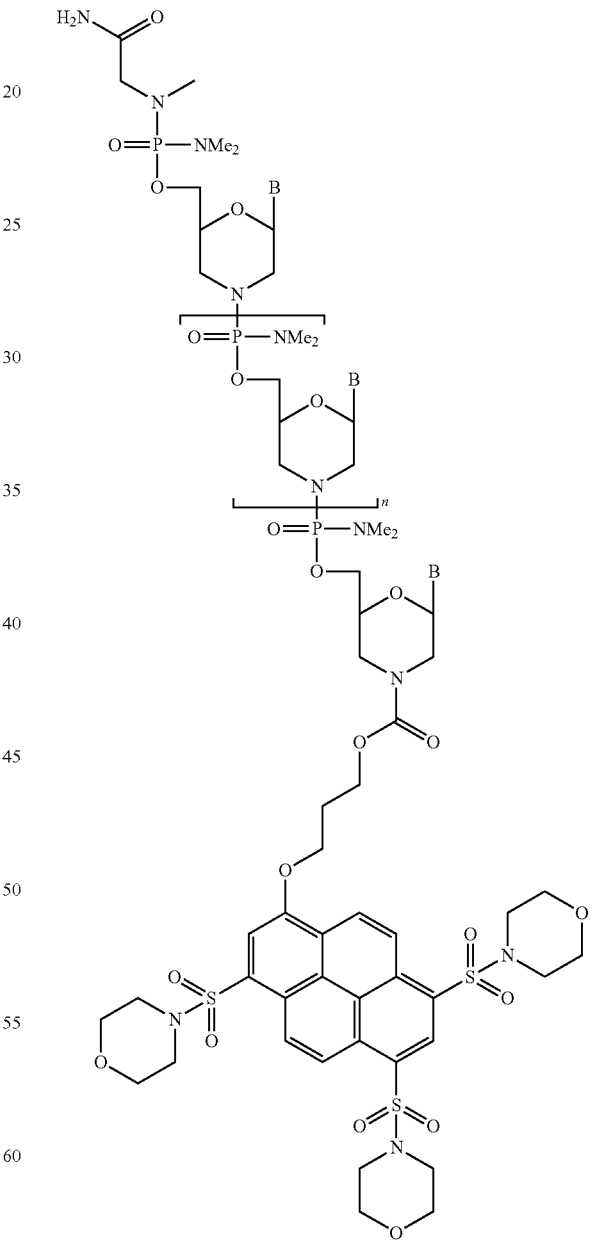

B = A (adenine)
C (cytosine)
G (guanine)
T (thymine)

What is claimed is:

1. A fluorescent dye having the structure:

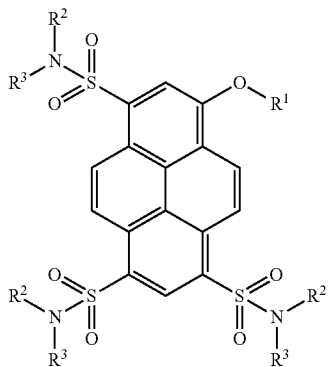

wherein,
(a) $R^1$ is a leash that contains a chemically reactive functional group to form a conjugate having a biologically active ligand and a biomolecule, wherein the chemically reactive functional group is activated ester, activated carbonate, acyl azides, acid halides, or other reactive groups that include acrylamides, alkyl and arylazides, alkynes and constrained cyclic alkynes, anhydrides, halides, sulfonate esters, amines, alcohols, haloacetamides, isothiocyanates and isocyanates; and
(b) $R^2$ and $R^3$ in sulfonamide are selected from an independent alkyl group which is methyl, ethyl, propyl, and cyclic rings with or without heteroatoms which are nitrogen, oxygen, sulfur, or phosphorus.

2. A fluorescent dye as recited in claim 1, wherein $R^1$ is a leash containing an activated carbonate, a sulfonamide moiety is N-sulfonylmorpholine, and the dye has the structure:

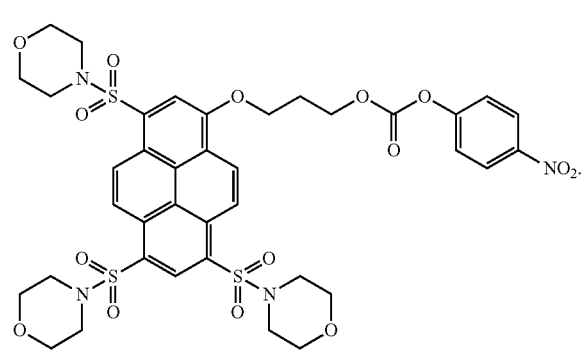 [SMILES: O=C(OCCCOc1cc(S(=O)(=O)N2CCOCC2)c2ccc3c(S(=O)(=O)N4CCOCC4)cc(S(=O)(=O)N4CCOCC4)c4ccc1c2c43)Oc1ccc([N+](=O)[O-])cc1]

3. A fluorescent dye as recited in claim 1 wherein $R^1$ is a leash containing an activated ester, a sulfonamide moiety is N-sulfonylmorpholine, and the dye has the structure:

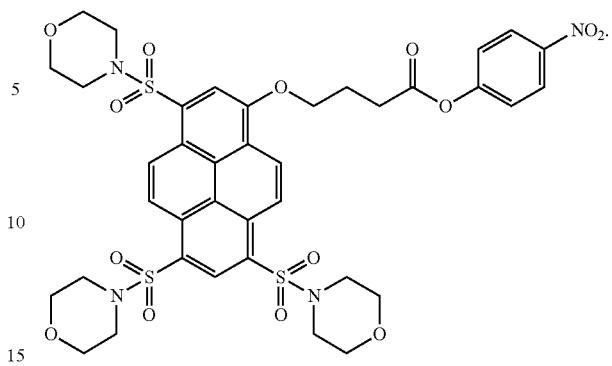

4. A fluorescent dye as recited in claim 1 wherein $R^1$ is a leash containing an amine, a sulfonamide moiety is N-sulfonylmorpholine, and the dye has the structure:

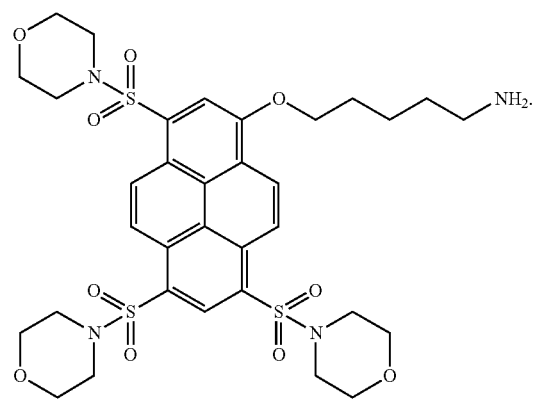 [SMILES: NCCCCCOc1cc(S(=O)(=O)N2CCOCC2)c2ccc3c(S(=O)(=O)N4CCOCC4)cc(S(=O)(=O)N4CCOCC4)c4ccc1c2c43]

5. A fluorescent dye as recited in claim 1 wherein $R^1$ is a leash containing an azide, a sulfonamide moiety is N-sulfonylmorpholine, and the dye has the structure:

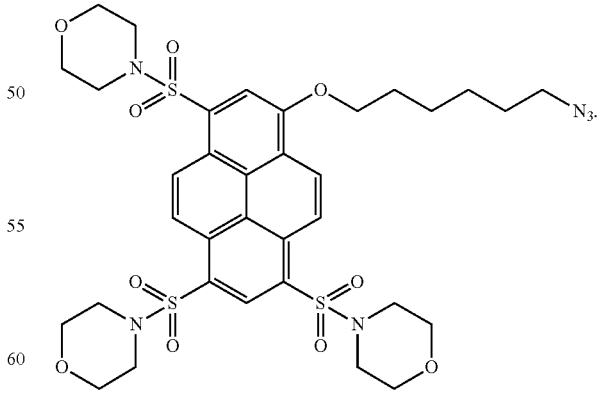

6. A fluorescent dye as recited in claim 1 wherein $R^1$ is a leash containing an alkyne, a sulfonamide moiety is N-sulfonylmorpholine, and the dye has the structure:

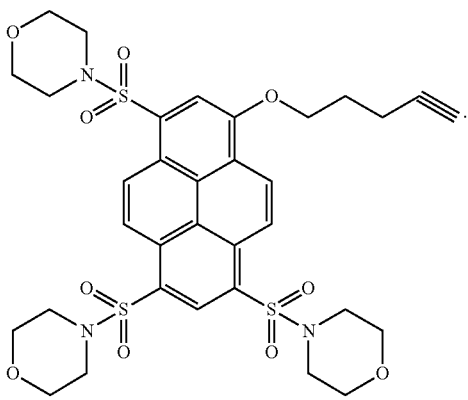 [SMILES: C#CCCCOc1cc(S(=O)(=O)N2CCOCC2)c2ccc3c(S(=O)(=O)N4CCOCC4)cc(S(=O)(=O)N4CCOCC4)c4ccc1c2c43]

7. A fluorescent dye as recited in claim 1 wherein R¹ is a leash containing a constrained cycloalkyne, a sulfonamide moiety is N-sulfonylmorpholine, and the dye has the structure:

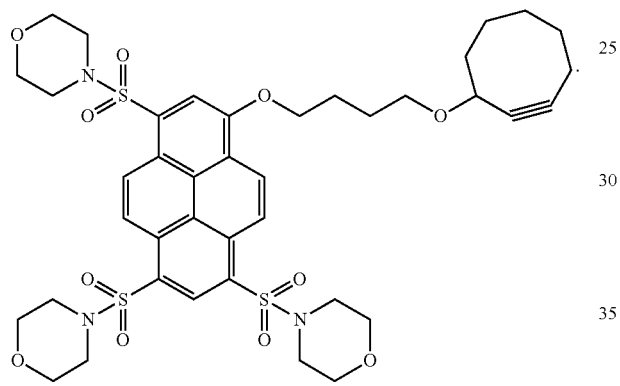

8. A fluorescent dye as recited in claim 1 wherein R¹ is an elongated leash containing an amine, a sulfonamide moiety is N-sulfonylmorpholine, and the dye has the structure:

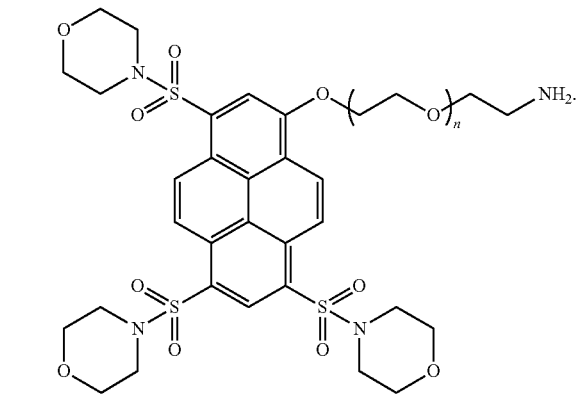

n = 1, 2, 3, or 4

9. A fluorescent dye as recited in claim 1 wherein the dye is conjugated with a biologically active ligand which is a cell, tissue, protein, antibody, enzyme, or a biomolecule which is a drug, hormone, nucleotide, nucleic acid, polysaccharide, lipid or other biomolecules which are natural or synthetic macromolecules or polymers.

10. A composition of claim 9, wherein a nucleotide is a Morpholino oligo.

11. A composition of claim 10, wherein a conjugate of the Morpholino oligo having the fluorescent dye has the structure:

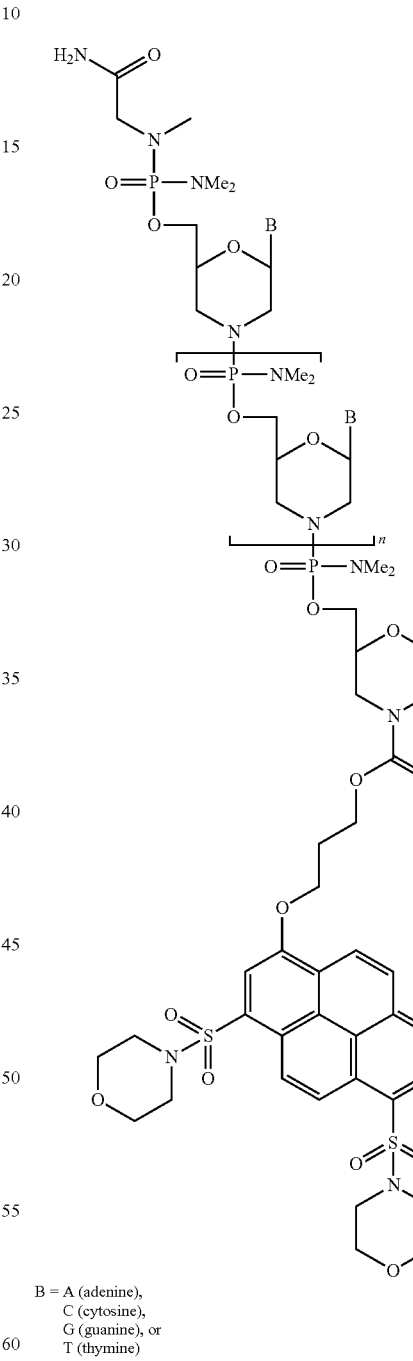

B = A (adenine),
C (cytosine),
G (guanine), or
T (thymine)

* * * * *